(12) United States Patent
Hartgrove et al.

(10) Patent No.: US 9,955,686 B2
(45) Date of Patent: May 1, 2018

(54) NONWOVEN FABRIC FOR INCREASING THE AVAILABILITY OF QUATERNARY AMMONIUM IN SOLUTION

(71) Applicant: AVINTIV Specialty Materials Inc., Charlotte, NC (US)

(72) Inventors: Herbert P. Hartgrove, Dunn, NC (US); Dianne B. Ellis, Cary, NC (US); Dawn Ellen Huston, Mooresville, NC (US); Teresa Ann Oldham, Erwin, NC (US)

(73) Assignee: AVINTIV Specialty Materials Inc., Charlotte, NC (US)

( * ) Notice: Subject to any disclaimer, the term of this patent is extended or adjusted under 35 U.S.C. 154(b) by 0 days. days.

(21) Appl. No.: 15/052,320

(22) Filed: Feb. 24, 2016

(65) Prior Publication Data
US 2016/0249606 A1 Sep. 1, 2016

Related U.S. Application Data

(60) Provisional application No. 62/121,057, filed on Feb. 26, 2015.

(51) Int. Cl.
| | |
|---|---|
| *A01N 25/22* | (2006.01) |
| *A01N 25/08* | (2006.01) |
| *A01N 33/12* | (2006.01) |
| *D06M 15/61* | (2006.01) |
| *A01N 25/10* | (2006.01) |
| *A01N 25/34* | (2006.01) |
| *A47L 13/17* | (2006.01) |
| *D04H 1/425* | (2012.01) |
| *D04H 1/492* | (2012.01) |
| *D04H 1/498* | (2012.01) |
| *D04H 3/16* | (2006.01) |
| *B32B 5/02* | (2006.01) |
| *B32B 5/06* | (2006.01) |
| *B32B 5/08* | (2006.01) |
| *B32B 5/26* | (2006.01) |
| *B32B 29/02* | (2006.01) |
| *B32B 7/04* | (2006.01) |
| *C11D 17/04* | (2006.01) |
| *D06M 13/46* | (2006.01) |

(52) U.S. Cl.
CPC ............. *A01N 25/22* (2013.01); *A01N 25/08* (2013.01); *A01N 25/10* (2013.01); *A01N 25/34* (2013.01); *A01N 33/12* (2013.01); *A47L 13/17* (2013.01); *B32B 5/022* (2013.01); *B32B 5/06* (2013.01); *B32B 5/08* (2013.01); *B32B 5/26* (2013.01); *B32B 7/04* (2013.01); *B32B 29/02* (2013.01); *C11D 17/04* (2013.01); *D04H 1/425* (2013.01); *D04H 1/492* (2013.01); *D04H 1/498* (2013.01); *D04H 3/16* (2013.01); *D06M 15/61* (2013.01); *B32B 2255/02* (2013.01); *B32B 2255/26* (2013.01); *B32B 2262/02* (2013.01); *B32B 2262/0253* (2013.01); *B32B 2262/0261* (2013.01); *B32B 2262/0276* (2013.01); *B32B 2262/06* (2013.01); *B32B 2262/14* (2013.01); *B32B 2307/718* (2013.01); *B32B 2307/7145* (2013.01); *B32B 2307/7166* (2013.01); *B32B 2307/724* (2013.01); *B32B 2307/726* (2013.01); *B32B 2432/00* (2013.01); *B32B 2555/00* (2013.01); *D06M 13/46* (2013.01)

(58) Field of Classification Search
CPC .... A01N 33/12; A01N 2300/00; A01N 25/34; A61K 31/568; A61K 31/5685; A61K 8/0208; A61L 2/16; A61L 2/232; A61L 2/235; A61Q 17/005

See application file for complete search history.

(56) References Cited

U.S. PATENT DOCUMENTS

| | | | |
|---|---|---|---|
| 5,006,125 A | 4/1991 | Patton et al. | |
| 5,330,541 A | 7/1994 | Hall et al. | |
| 5,667,533 A | 9/1997 | Hauser et al. | |
| 6,314,627 B1 | 11/2001 | Ngai | |
| 6,735,833 B2 | 5/2004 | Putnam et al. | |
| 6,903,034 B1 | 6/2005 | Putnam et al. | |
| 7,030,046 B2 * | 4/2006 | Wong ...................... | B08B 1/00 |
| | | | 15/1 |
| 7,091,140 B1 | 8/2006 | Ferencz et al. | |

(Continued)

FOREIGN PATENT DOCUMENTS

| | | |
|---|---|---|
| EP | 0992338 A2 | 4/2000 |
| WO | 2007070090 A1 | 6/2007 |

(Continued)

OTHER PUBLICATIONS

International Search Report and Written Opinion of corresponding application No. PCT/US2016/019501 dated Jul. 15, 2016, all enclosed pages cited.

(Continued)

*Primary Examiner* — Audrea Buckley

(74) *Attorney, Agent, or Firm* — McNair Law Firm, P.A.

(57) ABSTRACT

Wipes for preventing quaternary ammonium ("quat") depletion suitable for commercial applications (e.g., industrial and consumer disinfectant wipes) are provided. The wipe includes at least one nonwoven layer, at least one pulp layer, and a cationic additive. The at least one nonwoven layer and the at least one pulp layer may be hydroentangled to form a hydroentangled nonwoven fabric having a first surface and a second surface. Additionally, the cationic additive may be disposed on at least one of the first surface or the second surface.

16 Claims, 2 Drawing Sheets

(56) References Cited

U.S. PATENT DOCUMENTS

| | | | |
|---|---|---|---|
| 7,406,755 B2 | 8/2008 | Putnam et al. | |
| 7,455,800 B2 | 11/2008 | Ferencz et al. | |
| 2003/0054970 A1 | 3/2003 | Svendsen | |
| 2005/0155631 A1* | 7/2005 | Kilkenny | A47L 13/17 |
| | | | 134/6 |
| 2011/0081529 A1* | 4/2011 | Richeson | B32B 5/26 |
| | | | 428/212 |

FOREIGN PATENT DOCUMENTS

| | | | | |
|---|---|---|---|---|
| WO | WO2007/070090 A1 * | 6/2007 | | A61K 8/02 |
| WO | 2012107847 A2 | 8/2012 | | |
| WO | WO2012/107847 A2 * | 8/2012 | | A47L 13/17 |

OTHER PUBLICATIONS

Schill+Seilacher, SILASTOL® 186 F, report, May 9, 2014, pp. 1-8, SILASTOL_186_F.doc.
Astro American Chemical Co., Inc., A Better Reaction, technical bulletin, Nov. 20, 2014, pp. 1-5, Fountain Inn South Carolina, United States.
Second Written Opinion of the International Preliminary Examining Authority of corresponding International Application No. PCT/US2016/019501 dated Jan. 24, 2017.

* cited by examiner

210
Hydroentangling at least one nonwoven layer and at least one pulp layer to form a hydroentangled nonwoven fabric having a first surface and a second surface

220
Spraying a cationic additive onto at least one of the first surface or second surface from operation 210

FIG. 2

NONWOVEN FABRIC FOR INCREASING THE AVAILABILITY OF QUATERNARY AMMONIUM IN SOLUTION

PRIORITY CLAIM

This application claims priority under 35 U.S.C. § 119(e) to U.S. Provisional Application Ser. No. 62/121,057, filed on Feb. 26, 2015, which is expressly incorporated by reference herein in its entirety.

TECHNICAL FIELD

The presently-disclosed invention relates generally to wipes configured to prevent quaternary ammonium depletion having various commercial applications.

BACKGROUND

Commercial disinfectant wipes commonly employ quaternary ammonium ("quat") disinfectants. Quat-based disinfectants are effective disinfectants because they carry a positive charge, while bacteria, viruses, fungi and/or the like carry a negative charge. Accordingly, when a quat-based disinfectant wipe is applied to a surface, the charge of the bacterial cell changes from negative to positive, thereby disrupting the bacterial cell wall and eventually causing cell death. Some wipes incorporate the quat, while others allow consumers to use their own quat (e.g., liquid quat disinfectant solution) in conjunction with the wipes so that they may vary the quat concentration used. Regardless, some wipes have been found to deplete quat concentration in a disinfectant solution over time due to ionic chemical reactions between the fabric and the quat.

Therefore there at least remains a need in the art for a product that applies a cationic additive to fabric during manufacture to prevent a quat present in a disinfectant solution from attaching ionically to the wipe and depleting the quat concentration in the disinfectant solution.

SUMMARY OF INVENTION

One or more embodiments of the invention may address one or more of the aforementioned problems. Certain embodiments according to the invention provide wipes for preventing quaternary ammonium ("quat") depletion suitable for commercial applications (e.g., industrial and consumer disinfectant wipes). In one aspect, the wipe includes at least one nonwoven layer, at least one pulp layer, and a cationic additive. The at least one nonwoven layer and the at least one pulp layer may be hydroentangled together to form and/or define a hydroentangled nonwoven fabric having a first surface and a second surface. Furthermore, the cationic additive may be disposed on at least one of the first surface or the second surface.

In accordance with certain embodiments of the invention, the hydroentangled nonwoven fabric may comprise a first nonwoven layer and a second nonwoven layer. In such embodiments, the at least one pulp layer may be disposed between the first nonwoven layer and the second nonwoven layer. In other embodiments, the hydroentangled nonwoven fabric may comprise one nonwoven layer and one pulp layer.

In accordance with certain embodiments of the invention, the at least one nonwoven layer may comprise a spunbond layer. In some embodiments, the at least one nonwoven layer may comprise synthetic polymer filaments. In such embodiments, the synthetic polymer filaments may comprise at least one of a polyolefin, a polyester, a polyamide, or any combination thereof. According to certain embodiments, the synthetic polymer filaments may comprise at least one of polyethylene, polypropylene, partially aromatic or fully aromatic polyesters, polyhexamethylene diadipamide, polycaprolactam, aromatic or partially aromatic polyamides, aliphatic polyamides, or any combination thereof. In some embodiments, the synthetic polymer filaments may comprise polypropylene. In certain embodiments, the synthetic polymer filaments may have a denier comprising from about 0.5 to about 3. In further embodiments, the synthetic polymer filaments may have a denier comprising from about 1 to about 2.5.

In accordance with certain embodiments of the invention, the at least one pulp layer may comprise at least one of staple polymer fibers, organic pulp, synthetic pulp, meltblown fibers, or any combination thereof. In certain embodiments, the at least one pulp layer may comprise organic pulp. In such embodiments, the organic pulp may comprise cellulosic pulp. According to certain embodiments, the at least one pulp layer may comprise from about 1-99 percent by weight (or "wt %" as used herein) cellulosic pulp. In further embodiments, the at least one pulp layer may comprise from about 20-80 wt % cellulosic pulp. In other embodiments, the at least one pulp layer may comprise from about 40-60 wt % cellulosic pulp.

In accordance with certain embodiments of the invention, the hydroentangled nonwoven fabric may comprise from about 30-70 wt % of a polyolefin and from about 30-70 wt % of a cellulosic pulp. In other embodiments, the hydroentangled nonwoven fabric may comprise from about 45-55 wt % of a polyolefin and from about 45-55 wt % of a cellulosic pulp. In certain embodiments, the hydroentangled nonwoven fabric may comprise from about 30-70 wt % of a polypropylene and from about 30-70 wt % of a cellulosic pulp. In further embodiments, the hydroentangled nonwoven fabric may comprise from about 45-55 wt % of a polypropylene and from about 45-55 wt % of a cellulosic pulp. According to certain embodiments, the hydroentangled nonwoven fabric may have a basis weight comprising from about 10 to about 80 gsm. In further embodiments, the hydroentangled nonwoven fabric may have a basis weight comprising from about 20 to about 60 gsm. In other embodiments, the hydroentangled nonwoven fabric may have a basis weight comprising from about 30 to about 50 gsm. In certain embodiments, the hydroentangled nonwoven fabric may have a basis weight comprising about 40 gsm.

In accordance with certain embodiments of the invention, the cationic additive may comprise a cationic polymer. In such embodiments, the cationic polymer may define a cationic coating. In such embodiments, the cationic coating may comprise a basis weight from about 0.5 to about 5 gsm (e.g., on a dry basis). In further embodiments, the cationic coating may comprise a basis weight from about 1 to about 4 gsm. In other embodiments, the cationic coating may comprise a basis weight from about 1.5 to about 3 gsm. In certain embodiments, the cationic coating may comprise a basis weight of about 2 gsm. According to certain embodiments, the cationic polymer may comprise a water-soluble polymer. In some embodiments, the cationic polymer may comprise a cationic polyamine. In certain embodiments, the cationic polyamine may have a backbone comprising a cationic amine group. In other embodiments, the cationic polyamine may have at least one side chain comprising a cationic amine group.

In accordance with certain embodiments of the invention, the wipe may maintain a substantially constant quaternary ammonium concentration in a disinfectant solution when the wipe is disposed therein. In such embodiments, the cationic additive may prevent the quaternary ammonium from ionically attaching to the wipe. According to certain embodiments, the quaternary ammonium concentration in the disinfectant solution may have less than a 10% reduction over a four hour period. In further embodiments, the quaternary ammonium concentration in the disinfectant solution may have less than a 5% reduction over a four hour period. In other embodiments, the quaternary ammonium concentration in the disinfectant solution may have less than a 2% reduction over a four hour period. According to certain embodiments, the cationic additive may be applied to the hydroentangled nonwoven fabric via any one or more of a spray nozzle, a foam applicator, a pad, and/or a kiss roll.

In another aspect, certain embodiments of the invention provide a method for forming a wipe. The method may comprise hydroentangling at least one nonwoven layer and at least one pulp layer together to form a hydroentangled nonwoven fabric having a first surface and a second surface and spraying a cationic additive onto at least one of the first surface or the second surface. Alternatively, the cationic additive may be applied by a foam applicator, a pad, and a kiss roll either in addition to or instead of the spraying technique.

In accordance with certain method embodiments of the invention, the method may further comprise meltspinning a polymer composition and forming the at least one nonwoven layer. In some embodiments, the method may further comprise positioning the first surface of the hydroentangled nonwoven fabric directly or indirectly onto an image transfer device having a three-dimensional pattern and applying jets of fluid directly or indirectly to the second surface of the hydroentangled nonwoven fabric to impart a three-dimensional pattern onto the hydroentangled nonwoven fabric.

In accordance with certain method embodiments of the invention, the hydroentangled nonwoven fabric may comprise a first nonwoven layer and a second nonwoven layer. In such embodiments, the at least one pulp layer may be disposed between the first nonwoven layer and the second nonwoven layer. In other embodiments, the hydroentangled nonwoven fabric may comprise one nonwoven layer and one pulp layer.

In accordance with certain method embodiments of the invention, the at least one nonwoven layer may comprise a spunbond layer. In some embodiments, the at least one nonwoven layer may comprise synthetic polymer filaments. In such embodiments, the synthetic polymer filaments may comprise at least one of a polyolefin, a polyester, a polyamide, or any combination thereof. According to certain embodiments, the synthetic polymer filaments may comprise at least one of polyethylene, polypropylene, partially aromatic or fully aromatic polyesters, polyhexamethylene diadipamide, polycaprolactam, aromatic or partially aromatic polyamides, aliphatic polyamides, or any combination thereof. In some embodiments, the synthetic polymer filaments may comprise polypropylene. In certain embodiments, the synthetic polymer filaments may have a denier comprising from about 0.5 to about 3. In further embodiments, the synthetic polymer filaments may have a denier comprising from about 1 to about 2.5.

In accordance with certain method embodiments of the invention, the at least one pulp layer may comprise at least one of staple polymer fibers, organic pulp, synthetic pulp, meltblown fibers, or any combination thereof. In certain embodiments, the at least one pulp layer may comprise organic pulp. In such embodiments, the organic pulp may comprise cellulosic pulp. According to certain embodiments, the at least one pulp layer may comprise from about 1-99 wt % cellulosic pulp. In further embodiments, the at least one pulp layer may comprise from about 20-80 wt % cellulosic pulp. In other embodiments, the at least one pulp layer may comprise from about 40-60 wt % cellulosic pulp.

In accordance with certain method embodiments of the invention, the hydroentangled nonwoven fabric may comprise from about 30-70 wt % of a polyolefin and from about 30-70 wt % of a cellulosic pulp. In other embodiments, the hydroentangled nonwoven fabric may comprise from about 45-55 wt % of a polyolefin and from about 45-55 wt % of a cellulosic pulp. In certain embodiments, the hydroentangled nonwoven fabric may comprise from about 30-70 wt % of a polypropylene and from about 30-70 wt % of a cellulosic pulp. In further embodiments, the hydroentangled nonwoven fabric may comprise from about 45-55 wt % of a polypropylene and from about 45-55 wt % of a cellulosic pulp. According to certain embodiments, the hydroentangled nonwoven fabric may have a basis weight comprising from about 10 to about 80 gsm. In further embodiments, the hydroentangled nonwoven fabric may have a basis weight comprising from about 20 to about 60 gsm. In other embodiments, the hydroentangled nonwoven fabric may have a basis weight comprising from about 30 to about 50 gsm. In certain embodiments, the hydroentangled nonwoven fabric may have a basis weight comprising about 40 gsm.

In accordance with certain method embodiments of the invention, the cationic additive may comprise a cationic polymer. In such embodiments, the cationic polymer may define a cationic coating. In such embodiments, the cationic coating may comprise a basis weight from about 0.5 to about 5 gsm. In further embodiments, the cationic coating may comprise a basis weight from about 1 to about 4 gsm. In other embodiments, the cationic coating may comprise a basis weight from about 1.5 to about 3 gsm. In certain embodiments, the cationic coating may comprise a basis weight of about 2 gsm. According to certain embodiments, the cationic polymer may comprise a water-soluble polymer. In some embodiments, the cationic polymer may comprise a cationic polyamine. In certain embodiments, the cationic polyamine may have a backbone comprising a cationic amine group. In other embodiments, the cationic polyamine may have at least one side chain comprising a cationic amine group.

In accordance with certain method embodiments of the invention, the wipe may maintain a substantially constant quaternary ammonium concentration in a disinfectant solution when the wipe is disposed therein. In such embodiments, the cationic additive may prevent the quaternary ammonium from ionically attaching to the wipe. According to certain embodiments, the quaternary ammonium concentration in the disinfectant solution may have less than 10% reduction over a four hour period. In further embodiments, the quaternary ammonium concentration in the disinfectant solution may have less than 5% reduction over a four hour period. In other embodiments, the quaternary ammonium concentration in the disinfectant solution may have less than 2% reduction over a four hour period.

BRIEF DESCRIPTION OF THE DRAWINGS

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout and wherein:

FIG. 2 illustrates a process flow diagram for forming a wipe according to an embodiment of the invention.

DETAILED DESCRIPTION

Figure 1:
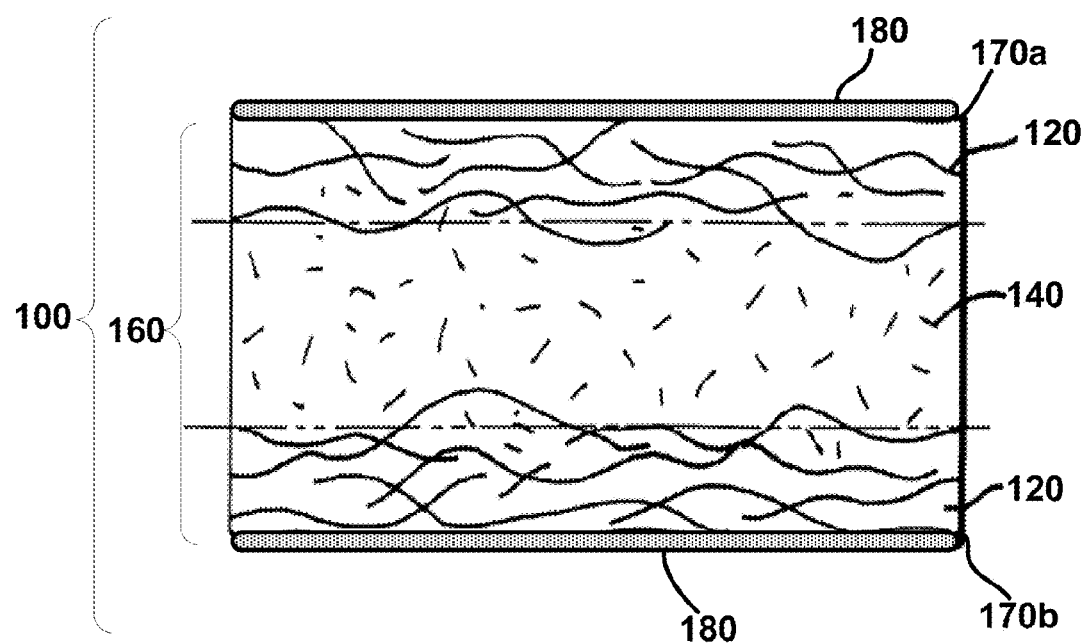
FIG. 1 illustrates a cross sectional view of a wipe according to an embodiment of the invention.

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Any relative dimensions illustrated in the figures are given by way of example and are not intended to be limiting. As would be appreciated by a person having ordinary skill in the art, the relative dimensions can vary depending on any number of factors including, without limitation, the intended use and performance of the illustrated article.

The invention includes, according to certain embodiments, a wipe based, at least in part, on at least one nonwoven layer and at least one pulp layer, such that the at least one nonwoven layer and the at least one pulp layer are hydroentangled together to form and/or define a hydroentangled nonwoven fabric having a first surface and a second surface. The invention also includes a cationic additive disposed on at least one of the first surface or the second surface. Wipes, according to certain embodiments of the invention, may prevent a quat present in a disinfectant solution from attaching ionically to the wipe and depleting the quat concentration in the disinfectant solution.

The terms "substantial" or "substantially" may encompass the whole amount as specified, according to certain embodiments of the invention, or largely but not the whole amount specified according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantionmers; and/or any chiral molecular configuration of such polymer or polymeric material. These configurations include, but are not limited to, isotactic, syndiotactic, and atactic configurations of such polymer or polymeric material.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process conventionally known in the art such as, for example, meltblowing processes, spunbonding processes, hydroentangling, air-laid, and bonded carded web processes.

The term "layer", as used herein, may comprise a generally recognizable combination of similar material types and/or functions existing in the X-Y plane.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous. It is noted that the spunbond used in certain composites of the invention may include nonwoven described in the literature as SPIN-LACE®.

The term "meltblown", as used herein, may comprise fibers formed by extruding a molten thermoplastic material through a plurality of fine die capillaries as molten threads or filaments into converging high velocity, usually hot, gas (e.g. air) streams which attenuate the filaments of molten thermoplastic material to reduce their diameter, which may be to microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Meltblown fibers are microfibers which may be continuous or discontinuous and are generally tacky when deposited onto a collecting surface.

The term "hydroentangle", as used herein, may comprise a process for bonding a nonwoven fabric by using high pressure water jets to intermingle the fibers. Several rows of water jets are directed against the fiber web, which is supported by a movable fabric. Fiber entanglements are introduced by the combined effects of the water jets and the turbulent water created in the web, which intertwines neighboring fibers.

The term "cellulosic pulp", as used herein, may comprise a variety of products comprising cellulose. Cellulose may refer to a natural carbohydrate polymer having the chemical formula $(C_5H_{10}O_5)_n$ and consisting of anhydro-glucose units joined by an oxygen linkage to form long molecular chains that are essentially linear. Natural sources of cellulose may comprise deciduous and coniferous trees (e.g., wood), cotton, flax, esparto grass, milkweed, straw, jute, hemp, and bagasse. The cellulose may have been processed by such treatments as, for example, thermal, chemical, and/or mechanical treatments to form cellulose pulp (e.g. wood pulp).

I. Wipe

In one aspect, the invention provides a wipe for preventing quaternary ammonium ("quat") depletion suitable for commercial applications (e.g., industrial and consumer disinfectant wipes). In one aspect, the wipe includes at least one nonwoven layer, at least one pulp layer, and a cationic additive. The at least one nonwoven layer and the at least one pulp layer may be hydroentangled together to form and/or define a hydroentangled nonwoven fabric having a first surface and a second surface. Furthermore, the cationic additive may be disposed on at least one of the first surface or the second surface.

In accordance with certain embodiments of the invention, for example, the wipe may maintain a substantially constant quaternary ammonium concentration in a disinfectant solution when the wipe is disposed therein. In such embodiments, for instance, the cationic additive may prevent the quaternary ammonium from ionically attaching to the wipe. In this regard, a disinfectant solution having a given quaternary ammonium concentration may not be substantially depleted over a given period of time. According to certain embodiments, for example, the cationic additive may be applied to the hydroentangled nonwoven fabric via a spray nozzle in order to prevent quaternary ammonium depletion in a disinfectant solution. In other embodiments of the invention, the cationic additive may be applied to the hydroentangled nonwoven fabric via a foam applicator. In yet other embodiments of the invention, the cationic additive may be applied to the hydroentangled nonwoven fabric via a pad. In still yet other embodiments of the invention, the cationic additive may be applied to the hydroentangled nonwoven fabric via a kiss roll.

According to certain embodiments of the invention, for instance, the quaternary ammonium concentration in the disinfectant solution may have less than a 10% reduction over a four hour period. In further embodiments, for example, the quaternary ammonium concentration in the disinfectant solution may have less than a 5% reduction over a four hour period. In other embodiments, for instance, the quaternary ammonium concentration in the disinfectant solution may have less than a 2% reduction over a four hour period. As such, in certain embodiments, the quaternary ammonium concentration in the disinfectant solution may have a reduction over a four hour period of less than the following: 10, 5, 4, 3, 2, and 1% (e.g., about 1-10%, about 1-5%, 1-2%, etc.).

In accordance with certain embodiments of the invention, for instance, the at least one nonwoven layer may comprise a spunbond layer. In certain embodiments, for example, the at least one nonwoven layer may be devoid of a meltblown layer. In some embodiments, for instance, the at least one nonwoven layer may comprise synthetic polymer filaments. In such embodiments, for example, the synthetic polymer filaments may comprise at least one of a polyolefin, a polyester, a polyamide, or any combination thereof. According to certain embodiments, for instance, the synthetic polymer filaments may comprise at least one of a polyethylene, a polypropylene, partially aromatic or fully aromatic polyesters, polyhexamethylene diadipamide, polycaprolactam, aromatic or partially aromatic polyamides, aliphatic polyamides, or any combination thereof. In some embodiments, for example, the synthetic polymer filaments may comprise polypropylene.

According to certain embodiments of the invention, for instance, the synthetic polymer filaments may have a denier comprising from about 0.5 to about 3. In further embodiments, for example, the synthetic polymer filaments may have a denier comprising from about 1 to about 2.5. As such, in certain embodiments, the synthetic polymer filaments may have a denier from at least about any of the following: 0.5, 0.75, and 1 and/or at most about 3, 2.75, and 2.5 (e.g., about 0.5-2.75, about 1-2.5, etc.).

In accordance with certain embodiments of the invention, for instance, the at least one pulp layer may comprise at least one of staple polymer fibers, organic pulp, synthetic pulp, meltblown fibers, or any combination thereof. In certain embodiments, for example, the at least one pulp layer may comprise organic pulp. In such embodiments, for instance, the organic pulp may comprise cellulosic pulp. In certain embodiments, for example, the at least one pulp layer may further comprise staple polymer fibers. In such embodiments, for instance, the staple polymer fibers may comprise acrylic fibers. Accordingly, in some embodiments, for example, the at least one pulp layer may comprise cellulosic pulp and/or acrylic fibers.

According to certain embodiments of the invention, for instance, the at least one pulp layer may comprise 100 wt % cellulosic pulp. In some embodiments, the at least one pulp layer may comprise from about 1-99 wt % cellulosic pulp. In further embodiments, for example, the at least one pulp layer may comprise from about 20-80 wt % cellulosic pulp. In other embodiments, for instance, the at least one pulp layer may comprise from about 40-60 wt % cellulosic pulp. As such, in certain embodiments, the at least one pulp layer may comprise cellulosic pulp at a weight percentage from at least about any of the following: 1, 10, 20, 25, 30, and 40 wt % and/or at most about 99, 85, 80, 75, 65, and 60 wt % (e.g., about 20-60 wt %, about 40-99 wt %, etc.).

In accordance with certain embodiments of the invention, for example, the cationic additive may comprise a cationic polymer. In certain embodiments, for instance, the cationic polymer may comprise a water-soluble polymer. In some embodiments, for example, the cationic polymer may comprise a cationic polyamine. In such embodiments, for example, the cationic polyamine may comprise a general structure represented by Formula I:

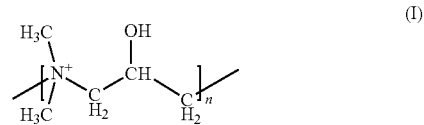

In certain embodiments, for instance, the cationic polyamine may have a backbone comprising a cationic amine group. In other embodiments, for example, the cationic polyamine may have at least one side chain comprising a cationic amine group. In further embodiments, for instance, the cationic additive may comprise a cationic polyamine blended with bis(hexamethylene)triamine (e.g., ASTRO FIX® 727 from Astro American Chemical Company, 557 South Woods Dr., Fountain Inn, S.C. 29644).

According to certain embodiments of the invention, for example, the cationic polymer may define a cationic coating. In such embodiments, for instance, the cationic coating may comprise a basis weight from about 0.5 to about 5 gsm (e.g., on a dry basis). In further embodiments, for instance, the cationic coating may comprise a basis weight from about 1 to about 4 gsm. In other embodiments, for example, the cationic coating may comprise a basis weight from about 1.5 to about 3 gsm. In certain embodiments, for instance, the cationic coating may comprise a basis weight of about 2 gsm. As such, in certain embodiments, the cationic coating may comprise a basis weight from at least about any of the following: 0.5, 1, 1.5, and 2 gsm and/or at most about 5, 4, 3, and 2 gsm (e.g., about 1.5-4 gsm, about 1-3 gsm, etc.).

In accordance with certain embodiments of the invention, for example, the hydroentangled nonwoven fabric may comprise a first nonwoven layer and a second nonwoven layer. In such embodiments, for instance, the at least one pulp layer may be disposed between the first nonwoven layer and the second nonwoven layer. In other embodiments, for example, the hydroentangled nonwoven fabric may comprise one nonwoven layer and one pulp layer. In certain embodiments, for instance, the hydroentangled nonwoven fabric may be a SPINLACE® nonwoven fabric as described in, for example, U.S. Pat. Nos. 6,903,034; 7,091,140; and 7,455,800, all of which are fully incorporated herein by reference.

According to certain embodiments of the invention, for example, the hydroentangled nonwoven fabric may comprise from about 30-70 wt % of one or more polyolefins and from about 30-70 wt % of one or more pulps (e.g., cellulosic pulp). In other embodiments, for instance, the hydroentangled nonwoven fabric may comprise from about 45-55 wt % of one or more polyolefins and from about 45-55 wt % of one or more pulps (e.g., cellulosic pulp). As such, in certain embodiments, the hydroentangled nonwoven fabric may comprise polyolefin and pulp (e.g., cellulosic pulp) at weight percentages from at least about any of the following: 30, 35, 40, and 45 wt % and/or at most about 70, 65, 60, and 55 wt % (e.g., about 40-60 wt %, about 45-55 wt %, etc.). In certain embodiments, for example, the hydroentangled nonwoven fabric may comprise from about 30-70 wt % of a polypropylene and from about 30-70 wt % of a cellulosic pulp. In further embodiments, for instance, the hydroentangled nonwoven fabric may comprise from about 45-55 wt % of a polypropylene and from about 45-55 wt % of a cellulosic pulp. As such, in certain embodiments, the hydroentangled nonwoven fabric may comprise polypropylene and cellulosic pulp at weight percentages from at least about any of the following: 30, 35, 40, and 45 wt % and/or at most about 70, 65, 60, and 55 wt % (e.g., about 40-60 wt %, about 45-55 wt %, etc.).

According to certain embodiments of the invention, for example, the hydroentangled nonwoven fabric may have a basis weight comprising from about 10 to about 80 gsm. In further embodiments, for instance, the hydroentangled nonwoven fabric may have a basis weight comprising from about 20 to about 60 gsm. In other embodiments, for example, the hydroentangled nonwoven fabric may have a basis weight comprising from about 30 to about 50 gsm. In certain embodiments, for instance, the hydroentangled nonwoven fabric may have a basis weight comprising about 40 gsm. As such, in certain embodiments, the hydroentangled nonwoven fabric may have a basis weight comprising from at least about any of the following: 10, 20, 30, and 40 gsm and/or at most about 80, 60, 50, and 40 gsm (e.g., about 20-50 gsm, about 40-50 gsm, etc.).

According to certain embodiments of the invention, for example, the hydroentangled nonwoven fabric may comprise at least one nonwoven layer having a basis weight from about 1 to about 20 gsm. In further embodiments, for instance, the hydroentangled nonwoven fabric may comprise at least one nonwoven layer having a basis weight from about 5 to about 15 gsm. In other embodiments, for example, the hydroentangled nonwoven fabric may comprise at least one nonwoven layer having a basis weight from about 7 to about 12 gsm. In certain embodiments, for instance, the hydroentangled nonwoven fabric may comprise at least one nonwoven layer having a basis weight of about 10 gsm. As such, in certain embodiments, the hydroentangled nonwoven fabric may comprise at least one nonwoven layer having a basis weight from at least about any of the following: 1, 5, 7, and 10 gsm and/or at most about 20, 15, 12, and 10 gsm (e.g., about 5-15 gsm, about 10-12 gsm, etc.).

According to certain embodiments of the invention, for example, the hydroentangled nonwoven fabric may comprise at least one pulp layer having a basis weight from about 5 to about 40 gsm. In further embodiments, for instance, the hydroentangled nonwoven fabric may comprise at least one pulp layer having a basis weight from about 10 to about 30 gsm. In other embodiments, for example, the hydroentangled nonwoven fabric may comprise at least one pulp layer having a basis weight from about 15 to about 25 gsm. In certain embodiments, for instance, the hydroentangled nonwoven fabric may comprise at least one pulp layer having a basis weight of about 20 gsm. As such, in certain embodiments, the hydroentangled nonwoven fabric may comprise at least one nonwoven layer having a basis weight from at least about any of the following: 5, 10, 15 and 20 gsm and/or at most about 40, 30, 25, and 20 gsm (e.g., about 5-25 gsm, about 20-25 gsm, etc.).

According to certain embodiments of the invention, for example, the hydroentangled nonwoven fabric may comprise, for example, an acrylic fiber layer disposed between a pulp layer and a nonwoven layer. In such embodiments, for instance, the pulp layer may comprise cellulosic pulp having a basis weight from about 1 to about 30 gsm. In further embodiments, for example, the pulp layer may comprise cellulosic pulp having a basis weight from about 10 to about 25 gsm. In other embodiments, for instance, the pulp layer may comprise cellulosic pulp having a basis weight from about 12 to about 18 gsm. In certain embodiments, for example, the pulp layer may comprise cellulosic pulp having a basis weight of about 15 gsm. As such, in certain embodiments, the pulp layer may comprise cellulosic pulp having a basis weight from at least about any of the following: 1, 10, 12, and 15 gsm and/or at most about 30, 25, 18, and 15 gsm (e.g., about 12-30 gsm, about 10-18 gsm, etc.). In some embodiments, for instance, the acrylic fiber layer may comprise a basis weight from about 0.5 to about 15 gsm. In further embodiments, for example, the acrylic fiber layer may comprise a basis weight from about 1 to about 10 gsm. In other embodiments, for instance the acrylic fiber layer may comprise a basis weight from about 3 to about 7 gsm. In certain embodiments, for example, the acrylic fiber layer may comprise a basis weight of about 5 gsm. As such, in certain embodiments, the acrylic fiber layer may comprise a basis weight from at least about any of the following: 0.5, 1, 3, and 5 gsm and/or at most about 15, 10, 7, and 5 gsm (e.g., about 3-15 gsm, about 5-7 gsm, etc.).

FIG. 1, for example, illustrates a cross sectional view of a wipe according to an embodiment of the invention. As shown in FIG. 1, the wipe 100 includes two nonwoven layers 120 and a pulp layer 140 that are hydroentangled to form a hydroentangled nonwoven fabric 160 having a first surface 170*a* and a second surface 170*b*. The wipe 100 also includes a cationic additive 180 disposed on the first surface 170*a* and the second surface 170*b*.

II. Method for Forming Wipe

In another aspect, the invention provides a method for forming a wipe. The method may comprise hydroentangling at least one nonwoven layer and at least one pulp layer together to form and/or define a hydroentangled nonwoven fabric having a first surface and a second surface and spraying a cationic additive onto at least one of the first surface or the second surface. In other embodiments of the invention, the cationic addition may be applied onto at least one of the first surface or the second surface by any one or more of applying via a foam applicator, a pad, and/or a kiss roll.

In accordance with certain embodiments of the invention, for instance, the method may further comprise meltspinning a polymer composition and forming the at least one nonwoven layer. In some embodiments, for example, the method may further comprise positioning the first surface of the hydroentangled nonwoven fabric directly or indirectly onto an image transfer device having a three-dimensional pattern and applying jets of fluid directly or indirectly to the second surface of the hydroentangled nonwoven fabric to impart a three-dimensional pattern onto the hydroentangled nonwoven fabric. For example, according to such embodiments, the image transfer device may comprise one or more drums or even one or more sleeves affixed to a corresponding drum. One or more water jets, for example, high pressure water jets according to an embodiment of the invention, may be applied to a side of the nonwoven opposite to the side contacting the image transfer device. Without intending to be bound by the theory, the one or more water jets and water directed through the nonwoven causes the fibers of the nonwoven to become displaced according to the image on the image transfer device such as the image formed on one or more drums or one or more sleeves affixed to a corresponding drum causing a three-dimensional pattern to be imaged throughout the nonwoven according to such image. Such imaging techniques are further described in, for example, U.S. Pat. No. 6,314,627 entitled "Hydroentangled Fabric having Structured Surfaces"; U.S. Pat. No. 6,735,833 entitled "Nonwoven Fabrics having a Durable Three-Dimensional Image"; U.S. Pat. No. 6,903,034 entitled "Hydroentanglement of Continuous Polymer Filaments"; U.S. Pat. No. 7,091,140 entitled "Hydroentanglement of Continuous Polymer Filaments"; and U.S. Pat. No. 7,406,755 entitled "Hydroentanglement of Continuous Polymer Filaments", each of which are included in their entirety herein by reference.

In accordance with certain embodiments of the invention, for instance, the at least one nonwoven layer may comprise a spunbond layer. In certain embodiments, for example, the at least one nonwoven layer may be devoid of a meltblown layer. In some embodiments, for instance, the at least one nonwoven layer may comprise synthetic polymer filaments. In such embodiments, for example, the synthetic polymer filaments may comprise at least one of a polyolefin, a polyester, a polyamide, or any combination thereof. According to certain embodiments, for instance, the synthetic polymer filaments may comprise at least one of a polyethylene, a polypropylene, partially aromatic or fully aromatic polyesters, polyhexamethylene diadipamide, polycaprolactam, aromatic or partially aromatic polyamides, aliphatic polyamides, or any combination thereof. In some embodiments, for example, the synthetic polymer filaments may comprise a polypropylene.

According to certain embodiments of the invention, for instance, the synthetic polymer filaments may have a denier comprising from about 0.5 to about 3. In further embodiments, for example, the synthetic polymer filaments may have a denier comprising from about 1 to about 2.5. As such, in certain embodiments, the synthetic polymer filaments may have a denier from at least about any of the following: 0.5, 0.75, and 1 and/or at most about 3, 2.75, and 2.5 (e.g., about 0.5-2.75, about 1-2.5, etc.).

In accordance with certain embodiments of the invention, for instance, the at least one pulp layer may comprise at least one of staple polymer fibers, organic pulp, synthetic pulp, meltblown fibers, or any combination thereof. In certain embodiments, for example, the at least one pulp layer may comprise organic pulp. In such embodiments, for instance, the organic pulp may comprise cellulosic pulp. In certain embodiments, for example, the at least one pulp layer may further comprise staple polymer fibers. In such embodiments, for instance, the staple polymer fibers may comprise acrylic fibers. Accordingly, in some embodiments, for example, the at least one pulp layer may comprise cellulosic pulp and/or acrylic fibers.

According to certain embodiments of the invention, for instance, the at least one pulp layer may comprise from about 1-99 wt % cellulosic pulp. In further embodiments, for example, the at least one pulp layer may comprise from about 20-80 wt % cellulosic pulp. In other embodiments, for instance, the at least one pulp layer may comprise from about 40-60 wt % cellulosic pulp. As such, in certain embodiments, the at least one pulp layer may comprise cellulosic pulp at a weight percentage from at least about any of the following: 1, 10, 20, 25, 30, and 40 wt % and/or at most about 99, 85, 80, 75, 65, and 60 wt % (e.g., about 20-60 wt %, about 40-99 wt %, etc.).

In accordance with certain embodiments of the invention, for example, the cationic additive may comprise a cationic polymer. In certain embodiments, for instance, the cationic polymer may comprise a water-soluble polymer. In some embodiments, for example, the cationic polymer may comprise a cationic polyamine. In such embodiments, for example, the cationic polyamine may comprise a general structure represented by Formula I as shown above. In certain embodiments, for instance, the cationic polyamine may have a backbone comprising a cationic amine group. In other embodiments, for example, the cationic polyamine may have at least one side chain comprising a cationic amine group. In further embodiments, for instance, the cationic additive may comprise a cationic polyamine blended with bis(hexamethylene)triamine (e.g., ASTRO FIX® 727 from Astro American Chemical Company, 557 South Woods Dr., Fountain Inn, S.C. 29644).

According to certain embodiments of the invention, for example, the cationic polymer may define a cationic coating. In such embodiments, for instance, the cationic coating may comprise a basis weight from about 0.5 to about 5 gsm (e.g., on a dry basis). In further embodiments, for instance, the cationic coating may comprise a basis weight from about 1 to about 4 gsm. In other embodiments, for example, the cationic coating may comprise a basis weight from about 1.5 to about 3 gsm. In certain embodiments, for instance, the cationic coating may comprise a basis weight of about 2 gsm. As such, in certain embodiments, the cationic coating may comprise a basis weight from at least about any of the following: 0.5, 1, 1.5, and 2 gsm and/or at most about 5, 4, 3, and 2 gsm (e.g., about 1.5-4 gsm, about 1-3 gsm, etc.).

In accordance with certain embodiments of the invention, for example, the hydroentangled nonwoven fabric may comprise a first nonwoven layer and a second nonwoven layer. In such embodiments, for instance, the at least one pulp layer may be disposed between the first nonwoven layer and the second nonwoven layer. In other embodiments, for example, the hydroentangled nonwoven fabric may comprise one nonwoven layer and one pulp layer. In certain embodiments, for instance, the hydroentangled nonwoven fabric may be a SPINLACE® nonwoven fabric as described in, for example, U.S. Pat. Nos. 6,903,034; 7,091,140; and 7,455,800 all of which are fully incorporated herein by reference.

According to certain embodiments of the invention, for example, the hydroentangled nonwoven fabric may comprise from about 30-70 wt % of one or more polyolefins and from about 30-70 wt % of one or more pulps (e.g., cellulosic pulp). In other embodiments, for instance, the hydroentangled nonwoven fabric may comprise from about 45-55 wt % of one or more polyolefins and from about 45-55 wt % of one or more pulps (e.g., cellulosic pulp). As such, in certain embodiments, the hydroentangled nonwoven fabric may comprise polyolefin and pulp (e.g., cellulosic pulp) at weight percentages from at least about any of the following: 30, 35, 40, and 45 wt % and/or at most about 70, 65, 60, and 55 wt % (e.g., about 40-60 wt %, about 45-55 wt %, etc.). In certain embodiments, for example, the hydroentangled nonwoven fabric may comprise from about 30-70 wt % of a polypropylene and from about 30-70 wt % of a cellulosic pulp. In further embodiments, for instance, the hydroentangled nonwoven fabric may comprise from about 45-55 wt % of a polypropylene and from about 45-55 wt % of a cellulosic pulp. As such, in certain embodiments, the hydroentangled nonwoven fabric may comprise polypropylene and cellulosic pulp at weight percentages from at least about any of the following: 30, 35, 40, and 45 wt % and/or at most about 70, 65, 60, and 55 wt % (e.g., about 40-60 wt %, about 45-55 wt %, etc.).

According to certain embodiments of the invention, for example, the hydroentangled nonwoven fabric may have a basis weight comprising from about 10 to about 80 gsm. In further embodiments, for instance, the hydroentangled nonwoven fabric may have a basis weight comprising from about 20 to about 60 gsm. In other embodiments, for example, the hydroentangled nonwoven fabric may have a basis weight comprising from about 30 to about 50 gsm. In certain embodiments, for instance, the hydroentangled nonwoven fabric may have a basis weight comprising about 40 gsm. As such, in certain embodiments, the hydroentangled nonwoven fabric may have a basis weight comprising from at least about any of the following: 10, 20, 30, and 40 gsm and/or at most about 80, 60, 50, and 40 gsm (e.g., about 20-50 gsm, about 40-50 gsm, etc.).

According to certain embodiments of the invention, for example, the hydroentangled nonwoven fabric may comprise at least one nonwoven layer having a basis weight from about 1 to about 20 gsm. In further embodiments, for instance, the hydroentangled nonwoven fabric may comprise at least one nonwoven layer having a basis weight from about 5 to about 15 gsm. In other embodiments, for example, the hydroentangled nonwoven fabric may comprise at least one nonwoven layer having a basis weight from about 7 to about 12 gsm. In certain embodiments, for instance, the hydroentangled nonwoven fabric may comprise at least one nonwoven layer having a basis weight of about 10 gsm. As such, in certain embodiments, the hydroentangled nonwoven fabric may comprise at least one nonwoven layer having a basis weight from at least about any of the following: 1, 5, 7, and 10 gsm and/or at most about 20, 15, 12, and 10 gsm (e.g., about 5-15 gsm, about 10-12 gsm, etc.).

According to certain embodiments of the invention, for example, the hydroentangled nonwoven fabric may comprise at least one pulp layer having a basis weight from about 5 to about 40 gsm. In further embodiments, for instance, the hydroentangled nonwoven fabric may comprise at least one pulp layer having a basis weight from about 10 to about 30 gsm. In other embodiments, for example, the hydroentangled nonwoven fabric may comprise at least one pulp layer having a basis weight from about 15 to about 25 gsm. In certain embodiments, for instance, the hydroentangled nonwoven fabric may comprise at least one pulp layer having a basis weight of about 20 gsm. As such, in certain embodiments, the hydroentangled nonwoven fabric may comprise at least one pulp layer having a basis weight from at least about any of the following: 5, 10, 15 and 20 gsm and/or at most about 40, 30, 25, and 20 gsm (e.g., about 5-25 gsm, about 20-25 gsm, etc.).

According to certain embodiments of the invention, for example, the hydroentangled nonwoven fabric may comprise, for example, an acrylic fiber layer disposed between a pulp layer and a nonwoven layer. In such embodiments, for instance, the pulp layer may comprise cellulosic pulp having a basis weight from about 1 to about 30 gsm. In further embodiments, for example, the pulp layer may comprise cellulosic pulp having a basis weight from about 10 to about 25 gsm. In other embodiments, for instance, the pulp layer may comprise cellulosic pulp having a basis weight from about 12 to about 18 gsm. In certain embodiments, for example, the pulp layer may comprise cellulosic pulp having a basis weight of about 15 gsm. As such, in certain embodiments, the pulp layer may comprise cellulosic pulp having a basis weight from at least about any of the following: 1, 10, 12, and 15 gsm and/or at most about 30, 25, 18, and 15 gsm (e.g., about 12-30 gsm, about 10-18 gsm, etc.). In some embodiments, for instance, the acrylic fiber layer may comprise a basis weight from about 0.5 to about 15 gsm. In further embodiments, for example, the acrylic fiber layer may comprise a basis weight from about 1 to about 10 gsm. In other embodiments, for instance the acrylic fiber layer may comprise a basis weight from about 3 to about 7 gsm. In certain embodiments, for example, the acrylic fiber layer may comprise a basis weight of about 5 gsm. As such, in certain embodiments, the acrylic fiber layer may comprise a basis weight from at least about any of the following: 0.5, 1, 3, and 5 gsm and/or at most about 15, 10, 7, and 5 gsm (e.g., about 3-15 gsm, about 5-7 gsm, etc.).

In accordance with certain embodiments of the invention, for example, the wipe may maintain a substantially constant quaternary ammonium concentration in a disinfectant solution when the wipe is disposed therein. In such embodiments, for instance, the cationic additive may prevent the quaternary ammonium from ionically attaching to the wipe.

According to certain embodiments of the invention, for instance, the quaternary ammonium concentration in the disinfectant solution may have less than a 10% reduction over a four hour period. In further embodiments, for example, the quaternary ammonium concentration in the disinfectant solution may have less than a 5% reduction over a four hour period. In other embodiments, for instance, the quaternary ammonium concentration in the disinfectant solution may have less than a 2% reduction over a four hour period. As such, in certain embodiments, the quaternary ammonium concentration in the disinfectant solution may have a reduction over a four hour period of less than the following: 10, 5, 4, 3, 2, and 1% (e.g., about 1-10%, about 1-5%, 1-2%, etc.).

FIG. 2, for example, illustrates a process flow diagram for forming a wipe according to an embodiment of the invention. As shown in FIG. 2, the method comprises hydroentangling at least one nonwoven layer and at least one pulp layer to form a hydroentangled nonwoven fabric having a first surface and a second surface at operation 210. The method further comprises applying a cationic additive onto at least one of the first surface or second surface from operation 210 at operation 220. In the applying step, the cationic additive may be applied using any one or more of a spray nozzle, a foam applicator, a pad, and a kiss roll.

Thus, the invention includes, in accordance with certain embodiments, a wipe based, at least in part, on at least one nonwoven layer and at least one pulp layer, such that the at least one nonwoven layer and the at least one pulp layer are hydroentangled to form a hydroentangled nonwoven fabric having a first surface and a second surface. The invention also includes a cationic additive disposed on at least one of the first surface or the second surface. Wipes, according to certain embodiments of the invention, may exhibit reduced quat depletion by applying a cationic additive to fabric during manufacture to prevent the quat from attaching ionically to the wipe and depleting the quat concentration of the disinfectant solution.

EXAMPLES

The present disclosure is further illustrated by the following examples, which in no way should be construed as being limiting. That is, the specific features described in the following examples are merely illustrative and not limiting.

Test Method

Basis weight of the following examples was measured in a way that is consistent with the ASTM test method D3776. The results were provided in units of mass per unit area in g/m² (gsm).

Example 1

In Example 1, three different wipes were made. Wipe A was made of a SPINLACE® nonwoven fabric having 10 gsm polypropylene spunbond face, 10 gsm polypropylene spunbond back, and 20 gsm cellulose pulp (Golden Isles® Fluff Pulp Grade 4823 from Georgia-Pacific Packaging, 133 Peachtree St., NE, Atlanta, Ga. 30303) between the two spunbond layers. Wipe B was made of the same SPINLACE® fabric as Wipe A but with 15 gsm cellulose pulp (Golden Isles® Fluff Pulp Grade 4823 from Georgia-Pacific Packaging, 133 Peachtree St., NE, Atlanta, Ga. 30303) and 5 gsm 100% acrylic fiber. Wipe C had the same composition as Wipe A but used a blue polypropylene spunbond face and back. The construction of Wipes A-C are summarized in Table 1.

TABLE 1

| WIPE | BASIS WEIGHT (gsm) | CONSTRUCTION |
| --- | --- | --- |
| A | 40 | 10 gsm SB PP face/10 gsm SP PP back/20 gsm Pulp |
| B | 40 | 10 gsm SB PP face/10 gsm SP PP back/15 gsm Pulp/ 5 gsm acrylic fiber |
| C | 40 | 10 gsm BLUE SB PP face/10 gsm BLUE SB PP back/20 gsm Pulp |

Example 2

In Example 2, wipes were tested to determine the effectiveness of a cationic additive disposed on the wipes in preventing quat depletion from a disinfectant solution containing a quat. The wipes that were tested had the same composition as Wipe A from Example 1. Wipe A was sprayed using a spray nozzle with a cationic additive made by adding water to 100 g ASTRO FIX® 727 (Astro American Chemical Company, 557 South Woods Dr., Fountain Inn, S.C. 29644) to make 2 L of additive. A control solution having a quat concentration of 230 ppm was compared to a quat solution having the same quat concentration and having an ASTRO FIX® 727-coated wipe submerged therein. The control solution and the wipe-containing solution were titrated over a period from 1 minute to 1 hour. As shown in Table 2, the wipe sprayed with the cationic additive maintained relatively constant quat concentration in the disinfectant solution, thereby demonstrating that the wipe prevents quat depletion of the disinfectant solution.

TABLE 2

| Time (minutes) | Control Solution Quat Concentration (ppm) | Wipe A + Cationic Additive Quat Concentration (ppm) |
| --- | --- | --- |
| 1 | 230 | 230 |
| 15 | 230 | 230 |
| 60 | 230 | 230 |

In this regard, the quat concentration of the disinfectant solution having the wipe submerged therein was not appreciably reduced even after 1 hour (e.g., less than 1% reduction).

Example 3

In Example 3, wipes were again tested to determine the effectiveness of a cationic additive in preventing quat depletion of a disinfectant solution due to the wipe. The wipes that were tested had the same composition as Wipe B from Example 1. Wipe B was sprayed using a spray nozzle with a cationic additive made by adding water to 100 g ASTRO FIX® 727 (Astro American Chemical Company, 557 South Woods Dr., Fountain Inn, S.C. 29644) to make 2 L of additive. A control solution having a quat concentration of 230 ppm was compared to a quat solution having the same quat concentration and having an ASTRO FIX® 727-coated wipe submerged therein. The control solution and the wipe-containing solution were titrated over a period from 1 minute to 1 hour. As shown in Table 3, the wipe sprayed with the cationic additive maintained relatively constant quat concentration in the disinfectant solution, thereby demonstrating that the wipe prevents quat depletion of the disinfectant solution.

TABLE 3

| Time (minutes) | Control Solution Quat Concentration (ppm) | Wipe B + Cationic Additive Quat Concentration (ppm) |
| --- | --- | --- |
| 1 | 230 | 210 |
| 15 | 230 | 210 |
| 60 | 230 | 210 |

In this regard, the quat concentration of the disinfectant solution having the wipe submerged therein was not appreciably reduced even after 1 hour (e.g., less than 10% reduction).

Example 4

In Example 4, wipes were again tested to determine the effectiveness of a cationic additive in preventing quat depletion of a disinfectant solution due to the wipe. The wipes that were tested had the same composition as Wipe C from Example 1. Wipe C was sprayed using a spray nozzle with a cationic additive made by adding water to 100 g ASTRO FIX® 727 (Astro American Chemical Company, 557 South Woods Dr., Fountain Inn, S.C. 29644) to make 2 L of additive. A control solution having a quat concentration of 220 ppm was compared to a quat solution having the same quat concentration and having an ASTRO FIX® 727-coated wipe submerged therein. The control solution and the wipe-containing solution were titrated over a period from 1 minute to 4 hours. As shown in Table 4, the wipe sprayed with the cationic additive maintained relatively constant quat concentration in the disinfectant solution, thereby demonstrating that the wipe prevents quat depletion of the disinfectant solution.

TABLE 4

| Time (minutes) | Control Solution Quat Concentration (ppm) | Wipe C + Cationic Additive Quat Concentration (ppm) |
|---|---|---|
| 1 | 220 | 215 |
| 15 | 220 | 230 |
| 60 | 220 | 210 |
| 240 | 220 | 210 |

In this regard, the quat concentration of the disinfectant solution having the wipe submerged therein was not appreciably reduced even after 4 hours (e.g., less than 5% reduction).

Example 5

In Example 5, wipes were again tested to determine the effectiveness of a cationic additive in preventing quat depletion of a disinfectant solution due to the wipe. The test wipe was prepared according to Examples 1 and 4. A control solution having a quat concentration of 803 ppm was compared to a quat solution having the same quat concentration and having an ASTRO FIX® 727-coated wipe submerged therein. The control solution and the wipe-containing solution were titrated over a period from 1 minute to 4 hours. As shown in Table 5, the wipe sprayed with the cationic additive maintained relatively constant quat concentration in the disinfectant solution, thereby demonstrating that the wipe prevents quat depletion of the disinfectant solution.

TABLE 5

| Time (minutes) | Control Solution Quat Concentration (ppm) | Wipe C + Cationic Additive Quat Concentration (ppm) |
|---|---|---|
| 1 | 803 | 818 |
| 15 | 803 | 793 |
| 60 | 803 | 793 |
| 240 | 803 | 798 |

In this regard, the quat concentration of the disinfectant solution having the wipe submerged therein was not appreciably reduced even after 4 hours (e.g., less than 1% reduction). Thus, the results demonstrate that the wipes do not appreciably scavenge the quat in solution.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A wipe for preventing quaternary ammonium depletion, comprising:
   (a) a first spunbond layer and a second spunbond layer, wherein the first spunbond layer, the second spunbond layer, or both comprises one or more polyolefins;
   (b) at least one pulp layer disposed between the first spunbond layer and the second spunbond layer, the at least one pulp layer comprising (i) pulp and (ii) acrylic meltblown fibers, acrylic staple fibers, or both, and wherein the at least one pulp layer, the first spunbond layer, and the second spunbond layer are hydroentangled together and define a hydroentangled nonwoven fabric having a first surface and a second surface; and
   (c) a cationic additive disposed on at least one of the first surface or the second surface.

2. The wipe according to claim 1, wherein the first spunbond layer, the second spunbond layer, or both comprise at least one of a polyolefin, a polyester, a polyamide, or any combination thereof.

3. The wipe according to claim 2, wherein the first spunbond layer, the second spunbond layer, or both comprise a polypropylene.

4. The wipe according to claim 1, wherein the first spunbond layer, the second spunbond layer, or both comprise individual filaments having a denier comprising from 0.5 to 3.

5. The wipe according to claim 1, wherein the at least one pulp layer comprises organic pulp, synthetic pulp, or any combination thereof.

6. The wipe according to claim 1, wherein the hydroentangled nonwoven fabric comprises from 30-70 wt % of a polyolefin and from 30-70 wt % of a cellulosic pulp.

7. The wipe according to claim 1, wherein the hydroentangled nonwoven fabric has a basis weight comprising from 10 to 80 gsm.

8. The wipe according to claim 1, wherein the cationic additive comprises a cationic polymer.

9. The wipe according to claim 8, wherein the cationic polymer defines a cationic coating, said cationic coating comprising a basis weight from 0.5 to 5 gsm.

10. The wipe according to claim 8, wherein the cationic polymer comprises a water-soluble polymer.

11. The wipe according to claim 8, wherein the cationic polymer comprises a cationic polyamine including a backbone comprising a cationic amine group.

12. The wipe according to claim 1, wherein the wipe maintains a substantially constant quaternary ammonium concentration in a disinfectant solution when the wipe is disposed therein.

13. The wipe according to claim 1, wherein the at least one pulp layer comprises pulp and acrylic meltblown fibers, wherein the acrylic meltblown fibers are discontinuous.

14. The wipe according to claim 1, wherein the at least one pulp layer comprises pulp and acrylic staple fibers.

15. The wipe according to claim 1, wherein the at least one pulp layer comprises (i) pulp, (ii) acrylic meltblown fibers, and (iii) acrylic staple fibers.

16. The wipe according to claim 1, wherein the first spunbond layer and the second spunbond layer each comprises one or more polyolefins such that the hydroentangled nonwoven fabric comprises (i) from 35-55 wt % of the one or more polyolefins; (ii) from about 35-55 wt % pulp; and (iii) the balance of the hydroentangled nonwoven fabric comprising (a) the cationic additive and (b) the acrylic meltblown fibers, acrylic staple fibers, or both.

* * * * *